(12) United States Patent
Shafiee Haji Abadi et al.

(10) Patent No.: US 8,659,297 B2
(45) Date of Patent: Feb. 25, 2014

(54) REDUCING NOISE IN MAGNETIC RESONANCE IMAGING USING CONDUCTIVE LOOPS

(75) Inventors: Shabnam Shafiee Haji Abadi, North Bethesda, MD (US); Thomas Herbert Frank, Crofton, MD (US)

(73) Assignee: Perinatronics Medical Systems, Inc., Crofton, MD (US)

( * ) Notice: Subject to any disclaimer, the term of this patent is extended or adjusted under 35 U.S.C. 154(b) by 0 days.

(21) Appl. No.: 13/406,015

(22) Filed: Feb. 27, 2012

(65) Prior Publication Data

US 2013/0221964 A1 Aug. 29, 2013

(51) Int. Cl.
*G01V 3/00* (2006.01)

(52) U.S. Cl.
USPC .......................................................... 324/318

(58) Field of Classification Search
USPC ................................. 324/300–322
See application file for complete search history.

(56) References Cited

U.S. PATENT DOCUMENTS

| | | | |
|---|---|---|---|
| 4,017,858 A | 4/1977 | Kuipers | |
| 4,310,243 A | 1/1982 | Brown et al. | |
| 4,537,200 A | 8/1985 | Widrow | |
| 4,665,368 A * | 5/1987 | Sugiyama et al. | 324/318 |
| 4,767,993 A * | 8/1988 | Hanawa | 324/318 |
| 4,893,626 A | 1/1990 | Henley et al. | |
| 4,920,318 A * | 4/1990 | Misic et al. | 324/318 |
| 4,991,580 A | 2/1991 | Moore | |
| 4,991,587 A | 2/1991 | Blakely | |
| 5,038,785 A | 8/1991 | Blakeley et al. | |
| 5,042,499 A | 8/1991 | Frank et al. | |
| 5,436,564 A | 7/1995 | Kreger | |
| 5,511,553 A | 4/1996 | Segalowitz | |
| 5,523,534 A | 6/1996 | Meister | |
| 5,526,813 A | 6/1996 | Yoshida | |
| 5,594,337 A * | 1/1997 | Boskamp | 324/318 |
| 5,910,728 A * | 6/1999 | Sodickson | 324/309 |
| 5,929,639 A * | 7/1999 | Doty | 324/318 |
| 5,939,883 A * | 8/1999 | Green et al. | 324/322 |
| 5,976,088 A * | 11/1999 | Urbano et al. | 600/443 |
| 5,986,453 A * | 11/1999 | Anderson et al. | 324/300 |
| 5,987,348 A | 11/1999 | Fischer | |
| 6,032,063 A | 2/2000 | Hoar | |
| 6,052,614 A | 4/2000 | Morris | |
| 6,054,855 A * | 4/2000 | Anderson | 324/318 |
| 6,070,097 A | 5/2000 | Kreger | |
| 6,198,962 B1 * | 3/2001 | Su | 600/422 |

(Continued)

OTHER PUBLICATIONS

Abacherli, R. et al., "Suppression of MR Gradient Artefacts on electrophysiological Signals Based on an Adaptive Real-time Filter with LMS Coefficient Updates", MAGMA, vol. 18, pp. 41-50, 2005, Springer, Germany.

(Continued)

*Primary Examiner* — Dixomara Vargas
(74) *Attorney, Agent, or Firm* — Buchanan Ingersoll & Rooney PC (57) ABSTRACT

A method of processing an electrical signal includes: capturing, via at least one main lead, an electrical signal; capturing, via at least one noise lead, a noise reference signal, wherein the at least one noise lead includes at least one conductive loop formed on a plane; receiving, by a processing device, the electrical signal and the noise reference signal; and processing, by the processing device, the electrical signal to cancel the noise reference signal from the electrical signal to obtain a processed electrical signal.

26 Claims, 7 Drawing Sheets

(56) References Cited

U.S. PATENT DOCUMENTS

| | | | |
|---|---|---|---|
| 6,201,981 B1 | 3/2001 | Yarita | |
| 6,229,310 B1* | 5/2001 | Green et al. | 324/318 |
| 6,335,617 B1 | 1/2002 | Osadchy et al. | |
| 6,437,567 B1* | 8/2002 | Schenck et al. | 324/318 |
| 6,493,572 B1* | 12/2002 | Su et al. | 600/422 |
| 6,534,982 B1 | 3/2003 | Jakab | |
| 6,556,012 B2* | 4/2003 | Yamashita | 324/318 |
| 6,567,685 B2* | 5/2003 | Takamori et al. | 600/410 |
| 6,701,178 B2* | 3/2004 | Su et al. | 600/422 |
| 6,751,496 B2* | 6/2004 | Su et al. | 600/422 |
| 6,954,068 B1* | 10/2005 | Takamori et al. | 324/318 |
| 6,984,981 B2* | 1/2006 | Tamez-Pena et al. | 324/309 |
| 6,998,841 B1* | 2/2006 | Tamez-Pena et al. | 324/302 |
| 7,039,455 B1 | 5/2006 | Brosovich | |
| 7,071,693 B2* | 7/2006 | Yasuhara | 324/319 |
| 7,187,169 B2* | 3/2007 | Clarke et al. | 324/307 |
| 7,230,429 B1* | 6/2007 | Huang et al. | 324/322 |
| 7,292,032 B1* | 11/2007 | Polzin | 324/306 |
| 7,391,213 B2* | 6/2008 | Watkins et al. | 324/318 |
| 7,446,528 B2* | 11/2008 | Doddrell et al. | 324/318 |
| 7,619,412 B2* | 11/2009 | Okamoto et al. | 324/318 |
| 7,755,355 B2* | 7/2010 | Polzin | 324/306 |
| 7,884,609 B2* | 2/2011 | Soutome et al. | 324/322 |
| 2001/0010464 A1* | 8/2001 | Takamori et al. | 324/304 |
| 2001/0022515 A1* | 9/2001 | Yamashita et al. | 324/300 |
| 2002/0133086 A1 | 9/2002 | Connelly et al. | |
| 2003/0107376 A1* | 6/2003 | Yasuhara | 324/318 |
| 2004/0015067 A1 | 1/2004 | Watson | |
| 2004/0225210 A1 | 11/2004 | Brosovich et al. | |
| 2006/0058629 A1* | 3/2006 | Warntjes et al. | 600/410 |
| 2006/0100506 A1* | 5/2006 | Halperin et al. | 600/424 |
| 2008/0054900 A1* | 3/2008 | Polzin | 324/309 |
| 2008/0144900 A1* | 6/2008 | Li et al. | 382/130 |
| 2008/0221433 A1* | 9/2008 | Doyle | 600/422 |
| 2009/0076369 A1* | 3/2009 | Mistretta | 600/407 |
| 2009/0163798 A1 | 6/2009 | Abbott et al. | |
| 2010/0185172 A1* | 7/2010 | Fabro | 604/500 |
| 2010/0198056 A1* | 8/2010 | Fabro et al. | 600/424 |
| 2010/0198208 A1* | 8/2010 | Napp et al. | 606/27 |
| 2011/0044524 A1* | 2/2011 | Wang et al. | 382/131 |
| 2012/0068704 A1* | 3/2012 | Popescu | 324/309 |

OTHER PUBLICATIONS

Felblinger, J. et al., "Electrocardiogram Acquisition During MR Examinations for Patient Monitoring and Sequence Triggering", Magnetic Resonance Medicine, vol. 32, pp. 523-529, 1994, Wiley-Liss Inc.

Felblinger, J. et al., "Restoration of Electrophysiological Signals Distorted by Inductive effects of Magnetic Field Gradients During MR Sequences", Magnetic Resonance in Medicine, vol. 44, pp. 715-721, 1999, University of Bern, Switzerland.

Fischer, S.E. et al., "Novel Real-time R-wave Detection Algorithm Based on the Vectorcardiogram for Accurate Gated Magnetic Resonance Acquisition", Magnetic Resonance in Medicine, vol. 42, pp. 361-370, 1991, William & Wilkins, Baltimore, MD.

Laudon, M.K. et al., "Minimizing interference from Magnetic Resonance Images During Electrocardiography", IEEE Transactions on Biomedical Engineering, vol. 45, No. 2, pp. 160-164, Feb. 1998, University of Wisconsin—Madison, WI.

Mossawir, B.J. et al., "On the Applicability of the LMS Algorithm to Gradient Noise Elimination from EKG Signals During an MRI Scan", Jul. 29, 2005, Stanford University, CA.

Odille, F. et al., "Noise Cancellation Signal Processing Method and computer System for Improved Real-Time Electrocardiogram artifact correction During MRI Data Acquisition, IEEE Transactions on Biomedical Engineering", vol. 54, No. 4, pp. 630-640, Apr. 2007, Institute of Electrical and Electronics Engineers, new York, NY.

Parker, J.M. et al., "Acquisition of Electrophysiological Signals During Magnetic Resonance Imaging", Sleep, vol. 22, No. 8, pp. 1125-1126, 1999, UCLA, Los Angeles, CA.

Van Genderingen, H.R. et al., "Carbon-Fiber electrodes and Leads for Electrocardiography During MR Imaging", Radiology, vol. 171, p. 872, 1989, Free University Hospital Amsterdam, The Netherlands.

Yelderman, M. et al., ECG Enhancement by Adaptive Cancellation of Electrosurgical Interference, IEEE Transactions on Biomedical Engineering, vol. BME-30, No. 7, Jul. 1983.

Guha, S., "Bioengineering in Reproduction Medicine," C CRC Press Boca Raton, FL, 1989, 2 pages.

Kreger, K.S. et al., "Biopotential Adaptive Filtering in an MR Environment," Paper presented at the SMRM 11th Annual Scientific Meeting, 1992, p. 661.

Extended Search Report from European Patent Office dated Jul. 5, 2013, issued in corresponding European Patent Application No. 13156941.0. (6 pages).

* cited by examiner

REDUCING NOISE IN MAGNETIC RESONANCE IMAGING USING CONDUCTIVE LOOPS

STATEMENT REGARDING FEDERALLY SPONSORED RESEARCH OR DEVELOPMENT

This invention was made with government support under Grant HL66791, awarded by the National Institutes of Health. The government has certain rights in the invention.

FIELD

The present disclosure relates to collecting and processing electrical signals, specifically methods and systems for reducing noise in magnetic resonance imaging using conductive loops.

BACKGROUND

Magnetic Resonance Imaging (MRI) has developed as an extremely important tool in the practice of diagnostic medicine. Performing a MRI scan of a human subject can provide a clear high resolution internal image of the human cardiovascular system for instance, and can help identify the current structure and function of a person's heart or blood vessels, for example.

MRI scans of the cardiovascular system, typically operate by collecting and measuring bio-potential signals, such as an electrocardiogram (ECG) signal. The ECG signal produces the rhythmical contractions of heart muscle pumping blood to the lungs and the body. For instance, the ECG signal can be used as a trigger for the MRI to produce images such that the heart can be imaged at the same point in its cyclic rhythm. A variety of machinery and components may be used in order to obtain and measure an ECG signal from a subject within a MRI scanner in order to obtain and process an image, such as an MRI scanner, wires, leads, connectors, and other components that conduct and generate electrical interference, or noise. Because ECG signals are typically low voltage signals, the presence of noise can be problematic for the collecting and measuring of ECG signals.

Within an MRI scanner, electrical magnetic noise may typically be collected and measured using special MRI compatible ECG leads for measuring electrical activity. For example, additional leads may be attached to a subject for the specific purpose of collecting and measuring noise only, or leads that typically collect and measure electrical signals (e.g., of the heart) may concurrently also collect and measure noise. However, traditional leads may be bulky, cumbersome and numerous, or may be otherwise unable to accurately measure overall electrical interference. Thus, there is a perceived opportunity to improve the lead arrangement and configuration used for collecting and measuring noise only reference signals in a magnetic resonance imager for better processing of measured electrical signals.

SUMMARY

The present disclosure provides for a method, apparatus and system for collecting and processing electrical signals within an MRI scanner, for example.

A method of collecting and processing an electrical signal includes: capturing, via at least one primary signal main lead, a primary electrical signal consisting of both signal and noise; capturing, via at least one noise only reference lead, a noise reference, wherein the at least one noise reference lead includes at least one conductive loop formed on a plane; receiving, by a conducting loop, the noise reference; and processing, by the processing device, the electrical signal to cancel the noise within the primary electrical signal to obtain a processed noise free electrical signal.

An apparatus and system for collecting and processing a primary electrical signal consisting of both signal and noise includes: at least one main primary signal lead configured to capture a primary electrical signal consisting of both signal and noise; at least one noise reference lead configured to capture a noise reference, the at least one noise reference lead includes at least one conductive loop formed on a plane; a conducting loop configured to receive the noise reference; and a processing device configured to cancel the noise within the primary electrical signal to obtain a processed electrical signal.

BRIEF DESCRIPTION OF THE DRAWING FIGURES

Exemplary embodiments are best understood from the following detailed description when read in conjunction with the accompanying drawings. It is emphasized that, according to common practice, the various features of the drawings are not to scale. On the contrary, the dimensions of the various features may be arbitrarily expanded or reduced for clarity. Included in the drawings are the following figures.

Further areas of applicability of the present disclosure will become apparent from the detailed description provided hereinafter. It should be understood that the detailed description of exemplary embodiments are intended for illustration purposes only and are, therefore, not intended to necessarily limit the scope of the disclosure.

DETAILED DESCRIPTION

Magnetic Resonance Imaging System

Figure 1:
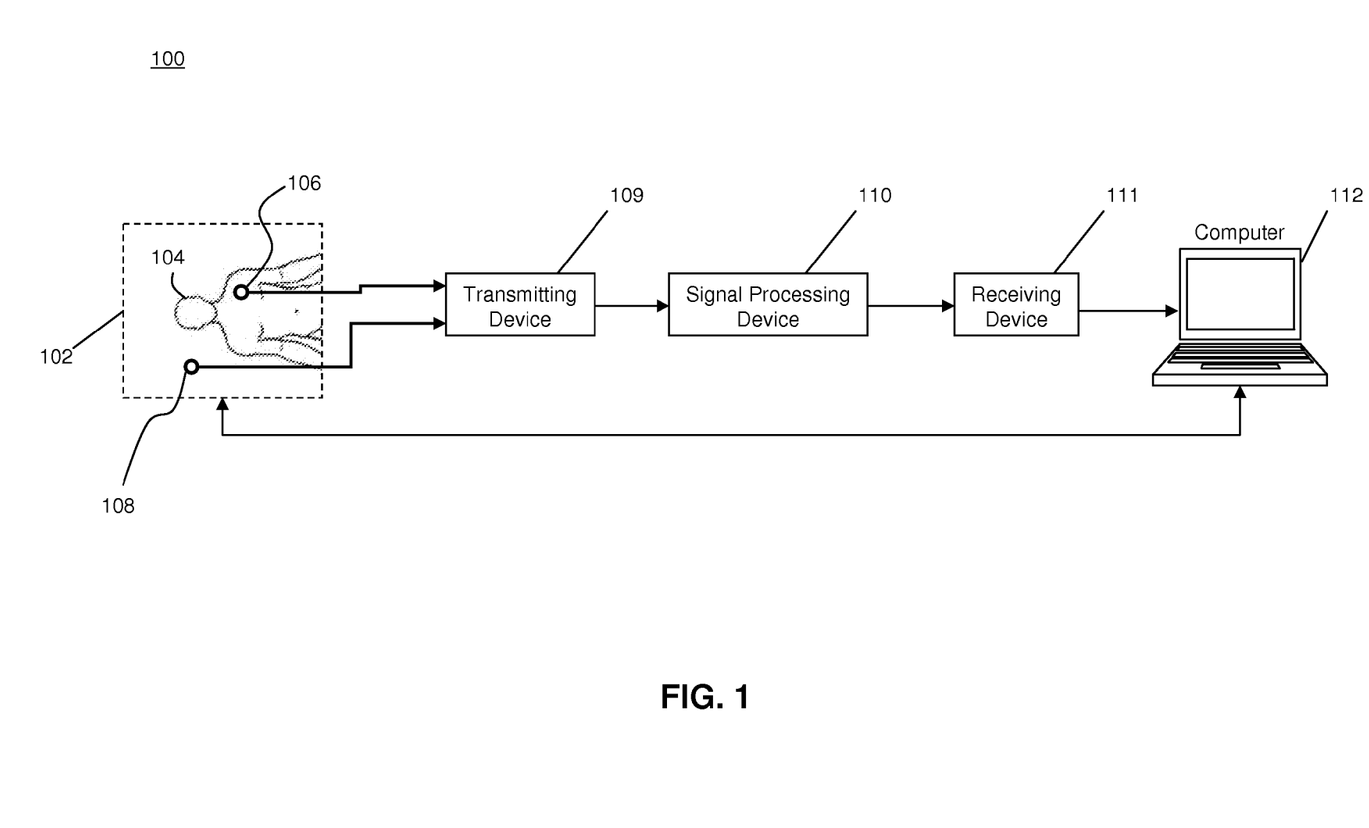
FIG. 1 is a block diagram illustrating a magnetic resonance imaging system in accordance with exemplary embodiments.

FIG. 1 illustrates a magnetic resonance imaging (MRI) system 100 for collecting and measuring electrical signals (e.g., an electrocardiogram signal) of a subject 104 within an MRI scanner and for collecting and measuring the electromagnetic noise produced by the MRI scanner per se.

The system 100 may include a MRI scanner 102, which may be configured to produce images of a subject 104, such as by using nuclear magnetic resonance (NMR) imaging techniques or other techniques as will be apparent to persons having skill in the relevant art. The subject 104 may be any subject that emits an electrical signal. In an exemplary embodiment, the subject 104 may be a human.

The subject 104 may be fitted with at least one lead 106 configured to capture an electrical signal and MRI generated noise reference. Separately, within the MRI scanner and not fitted to the subject, a conducting loop (e.g., a noise lead 108) may capture the MRI generated noise reference signal alone. In an exemplary embodiment, the subject 104 may be fitted with several leads 106 for capturing three respective electrical signals and separately three noise leads 108, not fitted to the subject, for capturing three respective noise references. The signal leads 106 and the noise leads 108 may be comprised of electrically conductive carbon filament wires with no metallic inclusions, as discussed in more detail below. In an exemplary embodiment, the noise leads 108 may include at least one conductive loop formed on a plane, as discussed in more detail below.

The signal leads 106 and the noise leads 108 may be connected to a signal processing device 110. In one embodiment, the connection may be via a transmitting device 109 configured to transmit at least electrical signals and noise reference (e.g., via a transmission medium, discussed in more detail below). In some embodiments, the transmitting device 109 may be included as part of the MRI scanner 102. In one embodiment, the transmitting device 109 may be part of a signal processing device (e.g., the transmitting unit 404 illustrated in FIG. 4). The signal processing device 110 may be any device configured to collect and process at least electrical signals and noise reference. The signal processing device 110 may also be configured to transmit the processed electrical signal to a receiving device 111. The receiving device 111 may be any device suitable for receiving the processed electrical signal, such as the computer 112, optical media, or any other external or internal receiving device. The signal processing device 110 may be any processing device capable of performing the functions as disclosed herein. In an exemplary embodiment, the signal processing device 110 may be included in the computer 112.

The computer 112 may be configured to generate and/or transmit a triggering signal to the MRI scanner 102. The MRI scanner 102 may receive the triggering signal in order to capture an image (e.g., using nuclear magnetic resonance) of the subject 104.

Noise Lead Configuration

Figure 2:
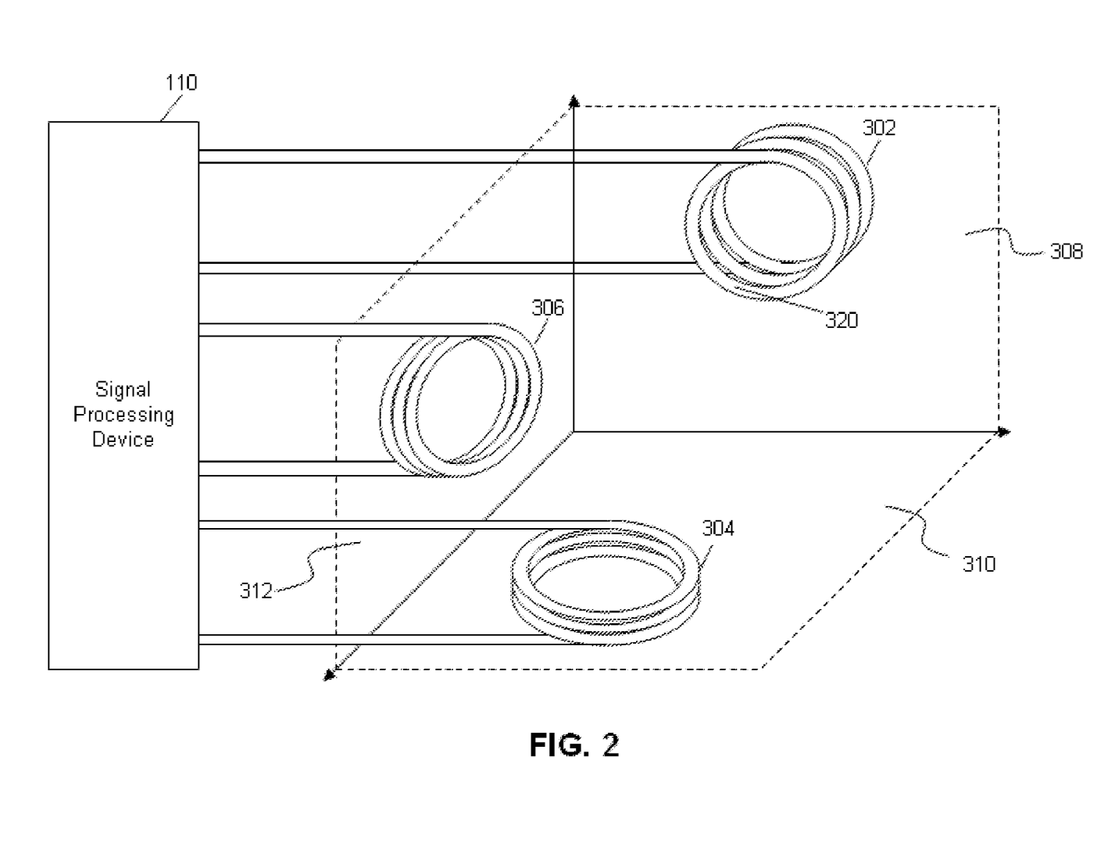
FIG. 2 is a diagram illustrating three noise only leads including conductive loops formed on three planes for capturing noise reference signals only in accordance with exemplary embodiments.

FIG. 2 illustrates greater detail of the noise lead 108, which may include a first noise lead 302, a second noise lead 304, and a third noise lead 306, each of which may include at least one conductive loop formed in separate distinct planes. For example, the first noise lead 302 may include three conductive loops as illustrated in FIG. 2, and may be formed in a first plane 308. In one embodiment, each noise lead may be formed on a plane unique to that noise lead. In a further embodiment, each plane may be orthogonally positioned relative to the other planes. For example, in FIG. 2, the first noise lead 302 may be formed on the first plane 308, the second noise lead 304 may be formed on a second plane 310, and the third noise lead 306 may be formed on a third plane 312, with planes 308, 310, and 312 being orthogonal to one another. Forming conductive loops with the noise leads may result in more accurate collection and measurement of MRI noise references. Using three noise leads oriented on three orthogonally positioned planes, as illustrated in FIG. 2, may further increase the accuracy of noise reference signals, which in turn may result in more accurate processed electrical signals.

Each of the noise leads 302, 304, and 306 may be connected to the signal processing device 110. In some embodiments, the noise leads 302, 304, and 306 may each be separately connected to a different lead or wire, which may be connected to the signal processing device 110. In an alternative embodiment, the noise leads 302, 304, and 306 may be connected in a series or parallel arrangement and then connected to the signal processing device. In an alternative embodiment, the noise lead 108 may include a single noise lead that includes at least two conductive loops (e.g., represented by the noise leads 302 and 304) that are orthogonally positioned. Other suitable configurations will be apparent to persons having skill in the relevant art.

Signal Processing Device and Computer

Figure 3:
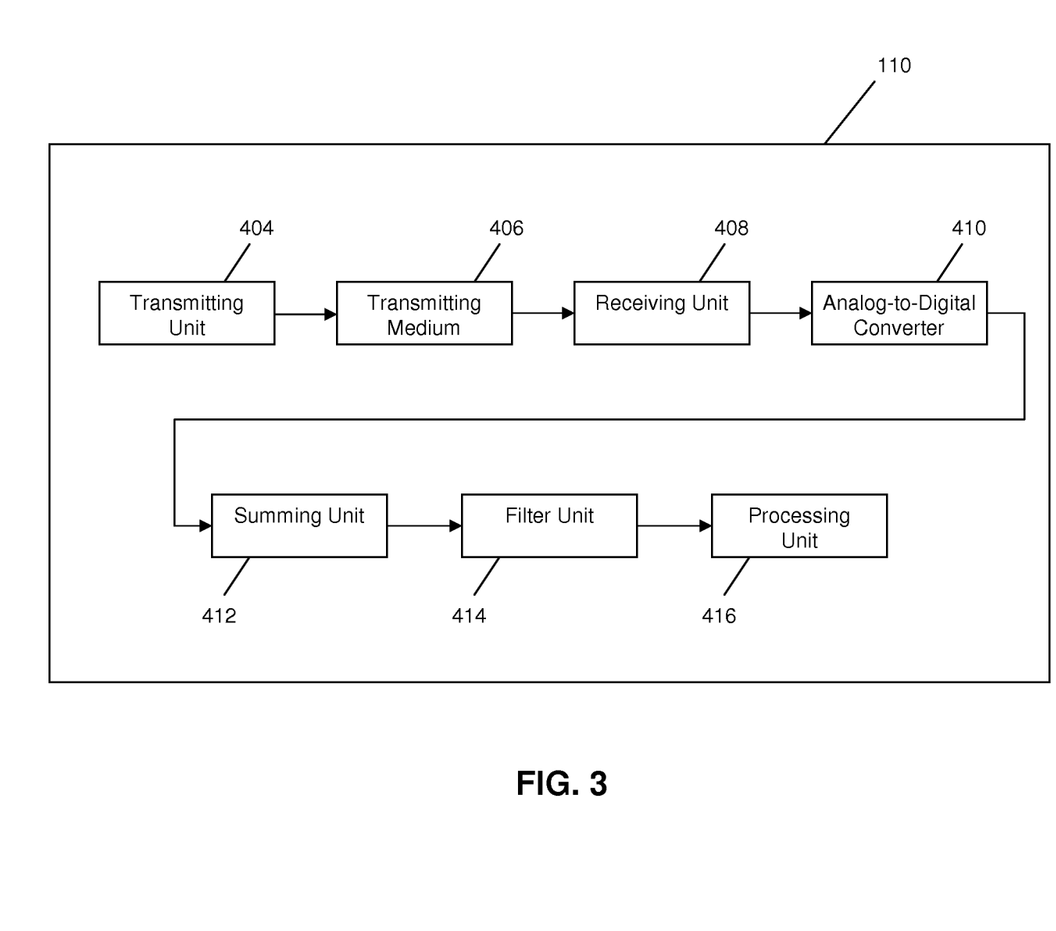
FIG. 3 is a block diagram illustrating a signal processing device in accordance with exemplary embodiments.

FIG. 3 illustrates a block diagram of the signal processing device 110. The signal processing device 110 may include a variety of components which may each be connected directly to one or more other components as further described below or via a bus that may be connected to any or all of the components. The configurations suitable for performing the functions as disclosed herein will be apparent to persons having skill in the relevant art.

The signal processing device 110 may include a transmitting unit 404 configured to transmit data. For example, the transmitting unit 404 may be configured to transmit electrical signals to the transmitting medium 406. For example, the transmitting unit 404 may be configured to transmit electrical signals containing noise and noise reference signals, such as from the signal leads 106 and the noise only leads 108. The transmission medium 406 may be any transmission medium suitable for performing the functions as disclosed herein, such as a fiber optic transmission medium or a wireless medium (e.g., Blue Tooth). The signal processing device 110 may further include a receiving unit 408 configured to receive data. For example, the receiving unit 408 may be configured to receive electrical signals containing noise and noise reference signals, such as from the signal leads 106 and the noise only leads 108.

The signal processing device 110 may also include an analog-to-digital converter 410. The analog-to-digital converter 410 may be configured to convert an analog signal, such as electrical signals from the leads 106 or noise reference signals from the noise leads 108, to a digital signal that may be processed by a processing unit 416. Methods of performing analog-to-digital conversions will be apparent to persons having skill in the relevant art.

The signal processing device 110 may further include a summing unit 412, which may be configured to add multiple signals together. For example, the summing unit 412 may be configured to sum together three noise reference signals (e.g., from the first noise lead 302, the second noise lead 304, and the third noise lead 306) into a single noise reference signal. The signal processing device 110 may also include a filter unit 414. The filter unit 414 may be configured to filter a signal (e.g., one or more electrical signals from the leads 106). The filter unit 414 may include at least one of a low pass filter, an adaptive filter, or any other type of filter suitable for performing functions as disclosed herein, as will be apparent to persons having skill in the relevant art.

The signal processing device 110 may also include the processing unit 416. The processing unit 416 may be configured to process received electrical signals, such as by processing adaptive filtering algorithms or GSO algorithms as discussed in more detail below. In some embodiments, the processing unit 416 and the filter unit 414 may be a single unit. In one embodiment, the signal processing device 110 may be included as part of the computer 112. In a further embodiment, only portions of the signal processing device 110 may be included in the computer 112. For example, the signal processing device 110 may not include its own individual processing unit 416, and may instead share a processing device 506 (illustrated in FIG. 4) with the computer 112, or the signal processing device 110 may not include the transmitting unit 404 or the transmitting medium 406.

Figure 4:
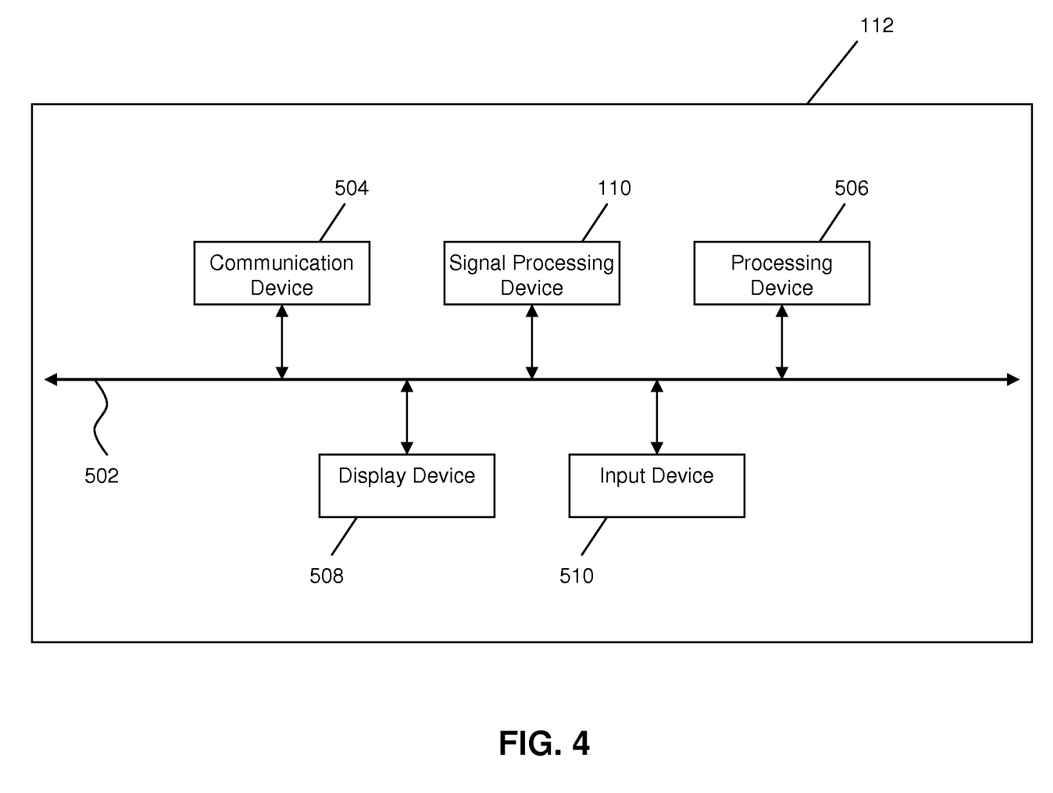
FIG. 4 is a block diagram illustrating a computer used for displaying processed ECG data for use to trigger the magnetic resonance scanner to produce images in accordance with exemplary embodiments.

FIG. 4 illustrates a block diagram of the computer 112. The computer 112 may include a variety of components which may each be connected via a bus 502. Bus types and configurations suitable for performing the functions as disclosed herein will be apparent to persons having skill in the relevant art.

The computer 112 may include a communication device 504. The communication device 504 may be configured to communicate (e.g., send or receive data) with other devices, such as the MRI scanner 102. In embodiments where the signal processing device 110 is not included as part of the computer 112, the communication device 504 may be configured to communicate with the signal processing device 110. In other embodiments, the communication device 504 may be configured to communicate with the leads 106 and the noise leads 108.

The computer 112 may also include a processing device 506. The processing device 506 may be configured to execute programs or software (e.g., stored in a memory, not shown) to cause the computer 112 to perform functions as disclosed herein. Suitable processing devices for use in the computer 112 will be apparent to persons having skill in the relevant art. The computer 112 may further include a display device 508, such as a monitor, which may be configured to display electrical signals that are noise free along with white spots produced by the processing algorithms at a time and place upon the electrocardiogram, for example, depicting the time of detection which is separately used to provide a trigger signal automatically to cause as MRI image scan to be taken. The computer 112 may also include an input device 510, such as a keyboard, mouse, etc., which may be configured to receive input from a user (e.g., a lab technician). For example, the user may use the input device 510 to instruct the computer 112 to transmit a trigger signal to the MRI scanner 102 to take an image of the subject 104.

Signal Processing Method and Algorithm

Figure 5:
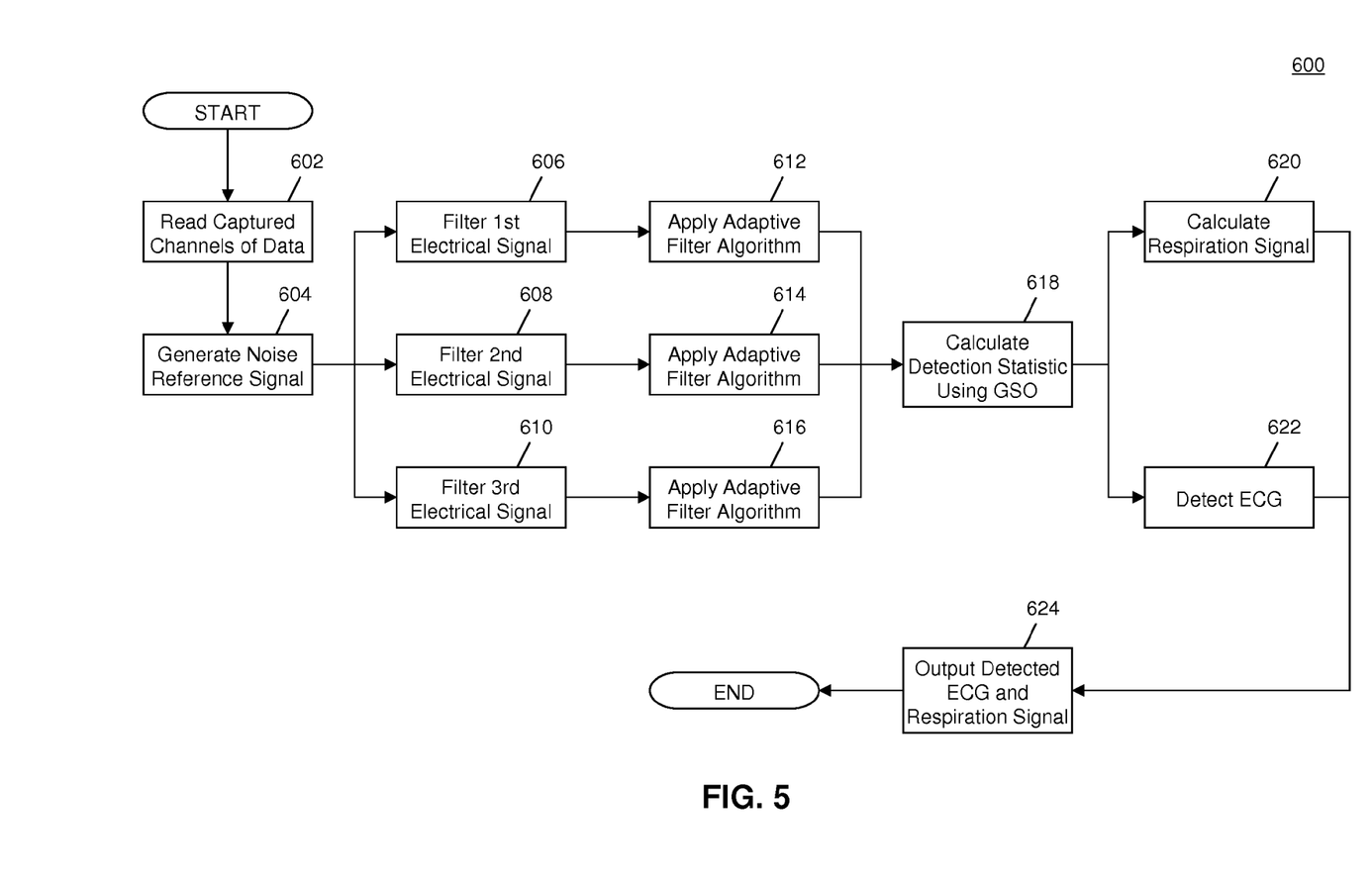
FIG. 5 is a flow chart illustrating a method for processing electrical signals using adaptive signal processing in accordance with exemplary embodiments.

FIG. 5 illustrates a method 600 for processing electrical signals (e.g., captured by the leads 106). The method 600 may be performed by a signal processing device, such as the signal processing device 110, which may be included as part of the computer 112 and/or connected to the MRI scanner 102. It should be understood that the method 600 is presented for illustration purposes only, and that other methods for processing electrical signals may be suitable as will be apparent to persons having skill in the relevant art.

In step 602, a signal processing device (e.g., the signal processing device 110) may read captured channels of data. In one embodiment, the captured channels of data may include three captured electrical signals (e.g., captured by three leads 106) and three captured noise reference signals (e.g., captured by the first noise lead 302, the second noise lead 304, and the third noise lead 306). In a further embodiment, the noise leads 302, 304, and 306 may each be formed on orthogonally positioned planes and include at least one conductive loop (e.g., conductive loop 320). In one exemplary embodiment, the three captured electrical signals may correspond to the frontal, sagittal, and coronal planes of the subject 104. In a further embodiment, the first, second, and third noise leads 302, 304, and 306 may each be formed on one of the frontal, sagittal, and coronal planes.

In step 604, the signal processing device 110 may generate a noise reference signal. The noise reference signal may be generated by adding together (e.g., using the summing unit 412) any received noise reference signals. In an exemplary embodiment, the noise reference signal is generated by adding together a first noise reference signal captured by the first noise lead 302, a second noise reference signal captured by the second noise lead 304, and a third noise reference signal captured by the third noise lead 306.

In steps 606, 608, and 612, first, second, and third electrical signals, respectively, may be filtered by the signal processing device 110. Filtering the electrical signals may include removing offset and filtering the electrical signal with a low pass filter (e.g., by using the generated noise reference signal). Offset removal methods and techniques and suitable low pass filters for filtering the electrical signals will be apparent to persons having skill in the relevant art. The filtered first, second, and third electrical signals may be used as the primary signal in an adaptive filtering algorithm in steps 612, 614, and 616, respectively. In an exemplary embodiment, the adaptive filtering algorithm is a least mean square (LMS) adaptive algorithm. LMS algorithms or other algorithm types suitable for filtering the electrical signals will be apparent to persons having skill in the relevant art.

The resulting first, second, and third electrical signals are used, in step 618, to calculate detection statistics. In an exemplary embodiment, a Gram-Schmidt Orthogonalization (GSO) algorithm may be used to calculate the detection statistics. An exemplary GSO algorithm may be as described in U.S. patent application Ser. No. 13/315,234, "ECG Triggered Heart and Arterial Magnetic Resonance Imaging," filed Dec. 8, 2011, which is herein incorporated by reference in its entirety. Other algorithms suitable for calculating detection statistics will be apparent to persons having skill in the relevant art. The detection statistics may be used to calculate a respiration signal (in step 620) and also may be used to detect electrocardiogram (ECG) signals (in step 622). In step 624, the signal processing device 110 (e.g., using the transmitting unit 404) may output the detected ECG and respiration signals (e.g., to the computer 112 or the processing device 506).

Figure 6:
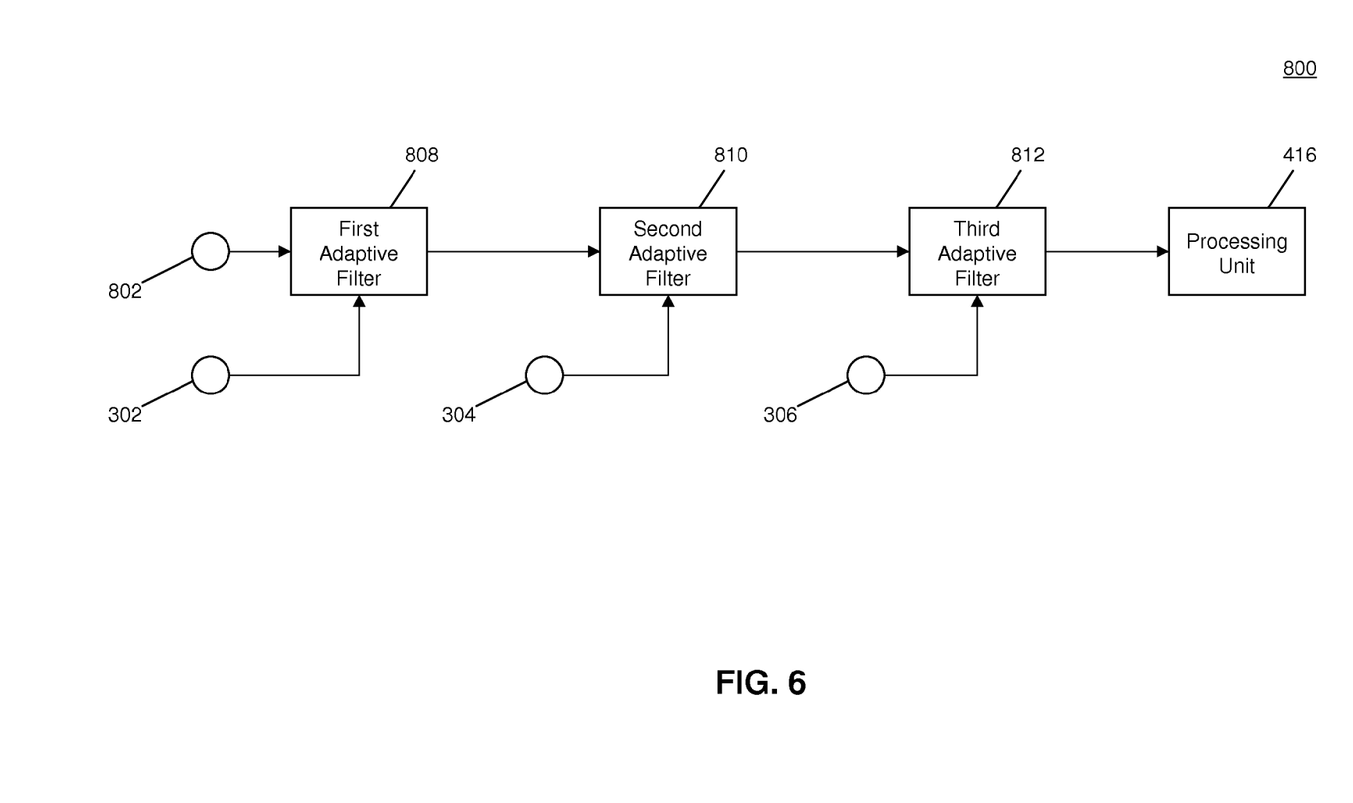
FIG. 6 is a block diagram illustrating a system of cascading adaptive filters for filtering captured electrical signals and noise reference signals.

FIG. 6 illustrates a block diagram of a system 800 of cascading adaptive filters, which may be used to filter an electrical signal using three noise reference signals for the generation of a filtered ECG signal. The system 800 may be used, for example, in steps 606-616 of FIG. 6. In some embodiments, the system 800 may operate as part of a signal processing device (e.g., as filter unit 414 of the signal processing device 110) or may be performed by a processor (e.g., such as the processing device 506 in the computer 112).

In the system 800, a first electrical signal captured by a first lead 802 (e.g., included in the leads 106 that may be fitted to the subject 104) may be input into a first adaptive filter 808. A first noise reference signal captured by the first noise lead 302 may also be input into the reference of the first adaptive filter 808. The first adaptive filter 808 may filter the captured first electrical signal using the noise reference signal, and output a first filtered signal.

The output of the first adaptive filter 808 may be connected to the (e.g., and received by) the primary input of a second adaptive filter 810. A second noise reference signal captured by the second noise lead 304 may also be input into the reference of the second adaptive filter 810. The second adaptive filter 810 may filter the first filtered signal using the second noise reference signal, and output a second filtered signal.

The output of the second adaptive filter 810 may be connected to the primary input of a third adaptive filter 812. The third adaptive filter 812 may also receive in its reference a third noise reference signal that may be captured by the third noise lead 306. The third adaptive filter 812 may filter the second filtered signal using the third noise reference signal to output a filtered electrical signal.

The filtered electrical signal may be output by the third adaptive filter 812 and may, in some embodiments, be transmitted to the processing unit 416 of the signal processing device 110. In other embodiments, the filtered electrical signal may be transmitted to the processing device 506 of the computer 112. The filtered electrical signal may be processed in such a way as to generate an ECG signal, which may be transmitted to the MRI scanner 102 (e.g., for the production of at least one image using NMR imaging).

Exemplary Method for Processing an Electrical Signal

Figure 7:
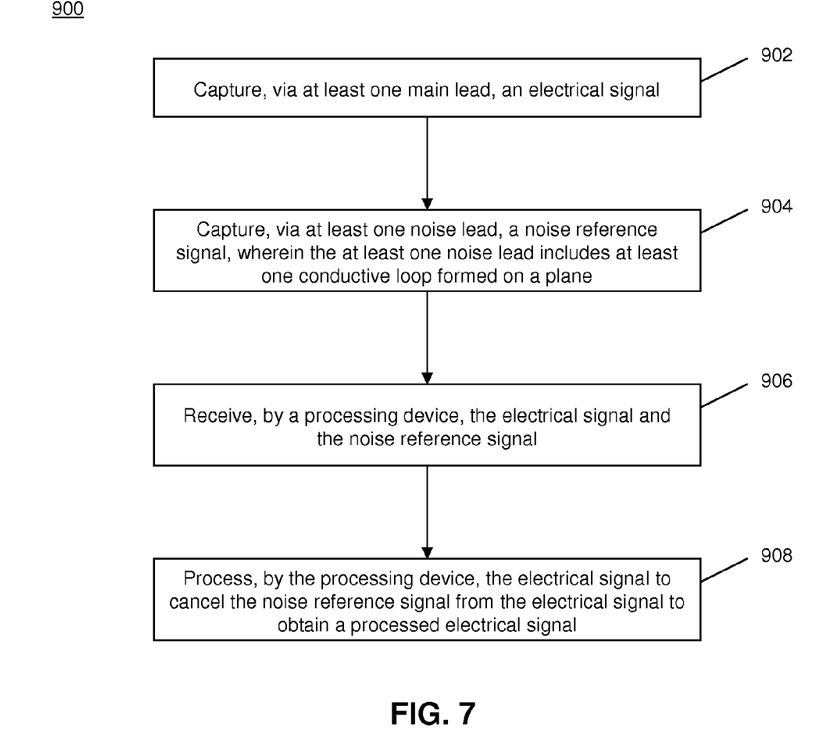
FIG. 7 is a flow chart illustrating an exemplary method for processing, producing and transmitting electrical signals to image the myocardium and cardiovascular system in accordance with exemplary embodiments.

FIG. 7 illustrates an exemplary method 900 for processing an electrical signal. In step 902, a processing device (e.g., the signal processing device 110) captures, via at least one main lead (e.g., a lead 106) an electrical signal. In one embodiment, an electrical signal is captured via three leads that capture three electrical signals that are summed together to form the electrical signal. In a further embodiment, each electrical signal is captured from one of the frontal, sagittal, and coronal planes of the body.

In step 904, the signal processing device 110 may capture, via at least one noise lead (e.g., noise lead 108), a noise reference signal, wherein the at least one noise lead includes at least one conductive loop (e.g., conductive loop 320) formed on a plane (e.g., the plane 308). In one embodiment, the at least one noise lead may include a first noise lead including a conductive loop formed on a first plane, a second noise lead including a conductive loop formed on a second plane, and a third noise lead including a conductive loop formed on a third plane, the first, second, and third planes not being parallel to one another. In a further embodiment, the first, second, and third planes are orthogonal. In another further embodiment, the first, second, and third noise reference signals from the respective first, second, and third noise leads may be summed together to form the noise reference signal. In an alternative embodiment, the at least one noise lead may include two or more orthogonally positioned conductive loops. In one embodiment, the at least one noise lead may include a carbon filament wire with no metallic inclusions.

In step 906, the signal processing device 110 may receive, by a processing device (e.g., the processing unit 416 of the signal processing device 110), the electrical signal and the noise reference signal. Then, in step 908, the processing unit 416 may process the electrical signal to cancel the noise reference signal from the electrical signal to obtain a processed electrical signal. In one embodiment, processing the electrical signal may include removing offset from the electrical signal, applying a low pass filter, applying an adaptive filter algorithm, and using a GSO algorithm to calculate detection statistics.

In one embodiment, the signal processing device 110 may also transmit (e.g., via the computer 112) the processed electrical signal as a trigger signal to a magnetic resonance imaging system (e.g., the MRI scanner 102) such that the magnetic resonance imaging system is able to capture at least one image based on the processed electrical signal.

Techniques consistent with the present disclosure provide, among other features, a method, apparatus and system for collecting and processing electrical signals within an MRI scanner. While various exemplary embodiments of the disclosed system and method have been described above it should be understood that they have been presented for purposes of example only, not limitations. It is not exhaustive and does not limit the disclosure to the precise form disclosed. Modifications and variations are possible in light of the above teachings or may be acquired from practicing of the disclosure, without departing from the breadth or scope.

What is claimed is:

1. A method of processing an electrical signal, comprising:
   transmitting, via at least one main lead, an electrical signal;
   capturing, via at least three noise leads, at least one noise reference signal as a measure of electromagnetic noise ambient to the at least one main lead;
   receiving, by a processing device, the electrical signal and the noise reference signal;
   processing, by the processing device, the electrical signal to cancel the noise reference signal from the electrical signal to obtain a processed electrical signal; and
   transmitting, by a transmitting device, the processed electrical signal as a trigger signal to a magnetic resonance imaging system, such that the magnetic resonance imaging system is able to capture at least one image based on the processed electrical signal,
   wherein the at least three noise leads includes
      a first noise lead including at least one conductive loop formed on a first plane,
      a second noise lead including at least one conductive loop formed on a second plane, and
      a third noise lead including at least one conductive loop formed on a third plane,
   wherein the first, second, and third planes are not parallel to one another.

2. The method of claim 1, wherein each of the at least three noise leads are orthogonally positioned and include at least three conductive loops.

3. The method of claim 1, wherein a first noise reference signal from the first noise lead, a second noise reference signal from the second noise lead, and a third noise reference signal from the third noise lead are summed together to form the noise reference signal.

4. The method of claim 1, wherein the electrical signal is an electrical signal indicative of motion of a moving element, wherein the moving element is at least one of a heart, blood vessel, or cardiovascular system.

5. The method of claim 1, wherein the at least one noise lead includes carbon filament wires with no metallic inclusions.

6. The method of claim 1, wherein processing the electrical signal to cancel the noise reference signal comprises:
   canceling a first noise reference signal captured from the first noise lead;
   canceling a second noise reference signal captured from the second noise lead; and
   canceling a third noise reference signal captured from the third noise lead.

7. The method of claim 1, wherein the electrical signal is emitted by a living being and reflective of a biological function.

8. The method of claim 7, wherein the electromagnetic noise is generated by a magnetic resonance imaging device.

9. The method of claim 8, wherein a first noise reference signal from the first noise lead, a second noise reference signal from the second noise lead, and a third noise reference signal from the third noise lead are summed together to form the noise reference signal.

10. The method of claim 8, wherein canceling the noise reference signal from the electrical signal comprises:
   canceling a first noise reference signal captured from the first noise lead;
   canceling a second noise reference signal captured from the second noise lead; and canceling a third noise reference signal captured from the third noise lead.

11. The method of claim 7, wherein the electrical signal is an echocardiogram signal or electroencephalogram signal.

12. The method of claim 7, wherein the at least one noise lead includes a first noise lead including at least one conductive loop formed on a first plane, a second noise lead including at least one conductive loop formed on a second plane, and a third noise lead including at least one conductive loop formed on a third plane, wherein the first, second, and third planes are not parallel to one another.

13. A system for processing an electrical signal, comprising:
    at least one main lead configured to transmit an electrical signal;
    at least three noise leads configured to capture at least one noise reference signal as a measure of electromagnetic noise ambient to the at least one main lead;
    a receiving device configured to receive the electrical signal and the noise reference signal; and
    a processor configured to cancel the noise reference signal from the electrical signal to obtain a processed electrical signal and cause a transmitting device to transmit the processed electrical signal to a magnetic resonance imaging system as a trigger signal, such that the magnetic resonance imaging system is able to capture at least one image based on the processed electrical signal,
    wherein the at least three noise leads includes
        a first noise lead including at least one conductive loop formed on a first plane,
        a second noise lead including at least one conductive loop formed on a second plane, and
        a third noise lead including at least one conductive loop formed on a third plane,
    wherein the first, second, and third planes are not parallel to one another.

14. The system of claim 13 wherein each of the at least three noise leads are orthogonally positioned and include at least three conductive loops.

15. The system of claim 13, wherein the processor is further configured to sum together a first noise reference signal from the first noise lead, a second noise reference signal from the second noise lead, and a third noise reference signal from the third noise lead to form the noise reference signal.

16. The system of claim 13, wherein the electrical signal is an electrical signal indicative of motion of a moving element, wherein the moving element is at least one of a heart, blood vessel, or cardiovascular system.

17. The system of claim 13, wherein the at least one noise lead includes carbon filament wires with no metallic inclusions.

18. The system of claim 13, wherein canceling the noise reference signal from the electrical signal comprises:
    canceling a first noise reference signal captured from the first noise lead;
    canceling a second noise reference signal captured from the second noise lead; and
    canceling a third noise reference signal captured from the third noise lead.

19. The system of claim 13, wherein the electrical signal is emitted by a living being and reflective of a biological function.

20. A method of processing an electrical signal, comprising:
    transmitting, via at least one main lead, an electrical signal emitted by a living being reflective of a biological function;
    capturing, via at least one noise lead, a noise reference signal as a measure of electromagnetic noise ambient to the at least one main lead, wherein the at least one noise lead includes at least one conductive loop formed on a plane;
    receiving, by a processing device, the electrical signal and the noise reference signal;
    processing, by the processing device, the electrical signal to cancel the noise reference signal from the electrical signal to obtain a processed electrical signal; and
    transmitting the processed electrical signal as a trigger signal to a magnetic resonance imaging system, such that the magnetic resonance imaging system is able to capture at least one image based on the processed electrical signal.

21. A system for processing an electrical signal, comprising:
    at least one main lead configured to transmit an electrical signal emitted by a living being and reflective of a biological function;
    at least one noise lead configured to capture a noise reference signal as a measure of electromagnetic noise ambient to the at least one main lead, wherein the at least one noise lead includes at least one conductive loop formed on a plane;
    a receiving device configured to receive the electrical signal and the noise reference signal; and
    a processor configured to cancel the noise reference signal from the electrical signal to obtain a processed electrical signal and transmit the processed electrical signal as a trigger signal to a magnetic resonance imaging system, such that the magnetic resonance imaging system is able to capture at least one image based on the processed electrical signal.

22. The system of claim 21, wherein the electrical signal is an echocardiogram signal or electroencephalogram signal.

23. The system of claim 21, wherein the electromagnetic noise is generated by a magnetic resonance imaging device.

24. The system of claim 21, wherein the at least one noise lead includes a first noise lead including at least one conductive loop formed on a first plane, a second noise lead including at least one conductive loop formed on a second plane, and a third noise lead including at least one conductive loop formed on a third plane, wherein the first, second, and third planes are not parallel to one another.

25. The system of claim 24, wherein a first noise reference signal from the first noise lead, a second noise reference signal from the second noise lead, and a third noise reference signal from the third noise lead are summed together to form the noise reference signal.

26. The system of claim 24, wherein canceling the noise reference signal from the electrical signal comprises:
    canceling a first noise reference signal captured from the first noise lead;
    canceling a second noise reference signal captured from the second noise lead; and
    canceling a third noise reference signal captured from the third noise lead.

* * * * *